(12) United States Patent
Murofushi et al.

(10) Patent No.: US 9,085,593 B2
(45) Date of Patent: Jul. 21, 2015

(54) THERAPEUTIC AGENT FOR ARTHROSIS

(71) Applicant: SANSHO CO., LTD., Tokyo (JP)

(72) Inventors: Kimiko Murofushi, Tokyo (JP); Ikuko Masuda, Tokyo (JP); Toshiro Morohoshi, Kanagawa (JP)

(73) Assignee: SANSHO CO., LTD., Tokyo (JP)

( * ) Notice: Subject to any disclaimer, the term of this patent is extended or adjusted under 35 U.S.C. 154(b) by 0 days.

(21) Appl. No.: 14/357,089

(22) PCT Filed: Oct. 12, 2012

(86) PCT No.: PCT/JP2012/076478
§ 371 (c)(1),
(2) Date: May 8, 2014

(87) PCT Pub. No.: WO2013/069404
PCT Pub. Date: May 16, 2013

(65) Prior Publication Data
US 2014/0309194 A1    Oct. 16, 2014

(30) Foreign Application Priority Data
Nov. 11, 2011   (JP) ................................ 2011-247047

(51) Int. Cl.
*A61K 31/662* (2006.01)
*A61K 31/661* (2006.01)
*C07F 9/6571* (2006.01)

(52) U.S. Cl.
CPC ......... *C07F 9/657163* (2013.01); *A61K 31/661* (2013.01); *A61K 31/662* (2013.01)

(58) Field of Classification Search
USPC ........................ 514/110, 120, 109; 558/82, 83
See application file for complete search history.

(56) References Cited

U.S. PATENT DOCUMENTS

| | | | |
|---|---|---|---|
| 7,550,449 B2 * | 6/2009 | Murofushi et al. | 514/109 |
| 2004/0204383 A1 * | 10/2004 | Tigyi et al. | 514/54 |
| 2004/0214799 A1 * | 10/2004 | Mukai et al. | 514/109 |

FOREIGN PATENT DOCUMENTS

| | | |
|---|---|---|
| JP | 07-149772 A | 6/1995 |
| JP | 2004-010582 A | 1/2004 |

OTHER PUBLICATIONS

Japanese version of International Preliminary report for application PCT/JP2012/076478, mail date is May 22, 2014.
English version of International Preliminary report for application PCT/JP2012/076478, mail date is Jun. 19, 2014.
International search report issued with respect to application PCT/JP2012/076478, mail date is Dec. 25, 2013.
New Zealand Office Action issued with respect to application No. 624870, mail date is Mar. 5, 2015.

* cited by examiner

*Primary Examiner* — Kristin Vajda
(74) *Attorney, Agent, or Firm* — Greenblum & Bernstein, P.L.C.

(57) ABSTRACT

This invention provides a therapeutic agent for arthrosis exerting inhibitory effects on articular cartilage destruction and high therapeutic effects on arthrosis. The invention provides a therapeutic agent for arthrosis which comprises, as an active ingredient, cyclic phosphatidic acid or carbacyclic phosphatidic acid.

4 Claims, 12 Drawing Sheets

A

B

C

D

THERAPEUTIC AGENT FOR ARTHROSIS

TECHNICAL FIELD

The present invention relates to a therapeutic agent for arthrosis comprising, as an active ingredient, cyclic phosphatidic acid or carbacyclic phosphatidic acid.

BACKGROUND ART

Arthrosis subtypes include, for example, osteoarthritis, articular rheumatism, and rheumatic fever, and the number of patients with osteoarthritis and articular rheumatism is particularly large. Accordingly, osteoarthritis and articular rheumatism are considered to be major arthrosis subtypes. Osteoarthritis is classified as congenital or secondary osteoarthritis or primary osteoarthritis caused by articular cartilage deformation resulting from aging. The number of patients with primary osteoarthritis is increasing as the elderly population increases. There are significant differences between osteoarthritis and articular rheumatism in terms of causes of diseases and clinical conditions, although these diseases have the following in common: Joint functions are impaired as a result of articular cartilage destruction at the end. To date, anti-inflammatory analgesic agents, such as aspirin and indomethacin, have been used as therapeutic agents for rheumatic diseases, such as osteoarthritis. However, such anti-inflammatory analgesic agents do not exert any inhibitory effects on articular cartilage destruction. In addition, the inhibitory effects of therapeutic agents such as gold preparations, immunosuppressive agents, and steroid preparations on articular cartilage destruction have not yet been confirmed in clinical settings.

Articular cartilage is composed of chondrocytes and cartilage matrices. Cartilage matrices have a complicated three-dimensional structure formed by collagens, which are fibrous proteins produced by chondrocytes, and proteoglycans (protein-polysaccharide complexes) bound to hyaluronic acids. Normal joint functions are maintained with the retention of a large quantity of water in the cartilage matrices.

In addition to the therapeutic agents for osteoarthritis described above, intraarticular injection of hyaluronic acid, which has been proven to have effects of protection and repair of articular cartilage and effects of lubrication in joints, has been employed in clinical settings. However, such technique is invasive and thus is not satisfactory from the viewpoint of patients' QOL.

SUMMARY OF THE INVENTION

Object to be Attained by the Invention

An object of the present invention is to provide a therapeutic agent for arthrosis which exerts inhibitory effects on articular cartilage destruction and high therapeutic effects on arthrosis.

Means for Attaining the Object

The present inventors considered that articular cartilage destruction may be inhibited by accelerating hyaluronic acid production in articular chondrocytes, and that it may function as an effective therapeutic means for osteoarthritis. They have conducted concentrated studies and, as a consequence, discovered that cyclic phosphatidic acids and derivatives thereof would accelerate hyaluronic acid production in chondrocytes derived from patients with osteoarthritis at significant levels, and that such effects would be observed in animal models of osteoarthrosis. This has led to the completion of the present invention.

Thus, the present invention provides a therapeutic agent for arthrosis which comprises, as an active ingredient, a compound represented by formula (I):

[Formula 1]

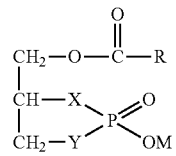

wherein R represents a linear or branched alkyl group having 1 to 30 carbon atoms, a linear or branched alkenyl group having 2 to 30 carbon atoms, or a linear or branched alkynyl group having 2 to 30 carbon atoms, which may contain a cycloalkane or aromatic ring; X and Y each independently represent an oxygen atom or a methylene group, provide that X and Y do not simultaneously represent a methylene group; and M represents a hydrogen atom or an alkali metal atom.

Preferably, in Formula (I), X and Y represent an oxygen atom.

Preferably, in Formula (I), either X or Y represents an oxygen atom and the other represents a methylene group.

Preferably, the compound represented by Formula (I) is carbacyclic phosphatidic acid of 1-oleoyl-cyclic phosphatidic acid, 1-palmitoleoyl-cyclic phosphatidic acid, or a derivative thereof.

The present invention further provides a method for treatment of arthrosis comprising administering a compound represented by the aforementioned Formula (I) to a patient with arthrosis.

The present invention further provides use of a compound represented by the aforementioned Formula (I) for production of a therapeutic agent for arthrosis.

Effects of the Invention

The present invention can provide a therapeutic agent for arthrosis which inhibits articular cartilage destruction and has high therapeutic effects on arthrosis.

EMBODIMENTS FOR CARRYING OUT THE INVENTION

Figure 1:
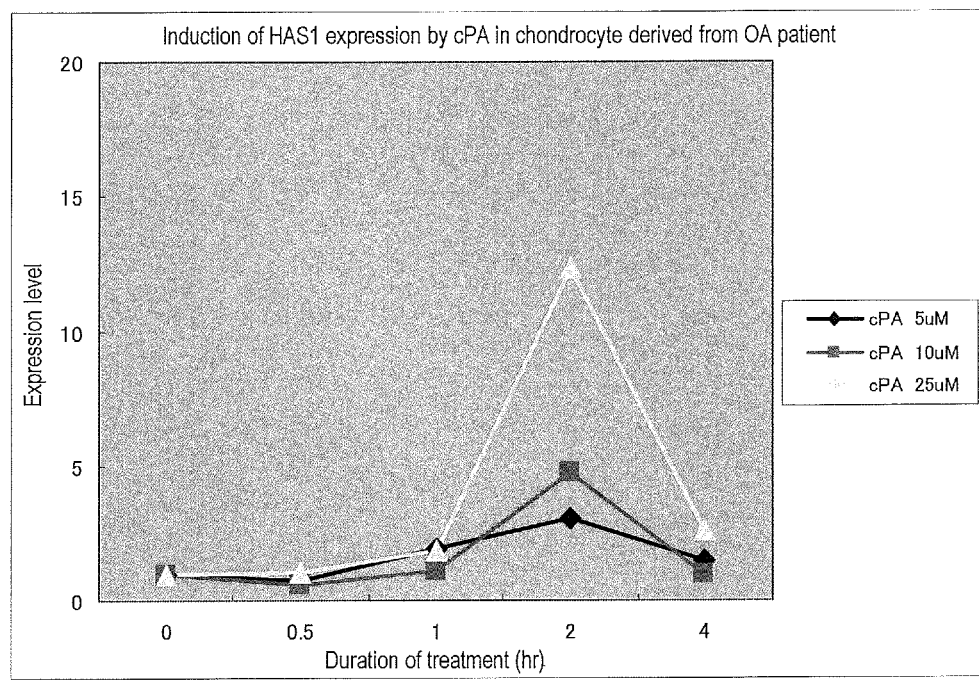
FIG. 1 shows the results of examination of effects of a cyclic phosphatidic acid derivative on expression of the hyaluronic acid synthase gene (HAS1) in chondrocytes derived from a patient with osteoarthritis.
Figure 1:
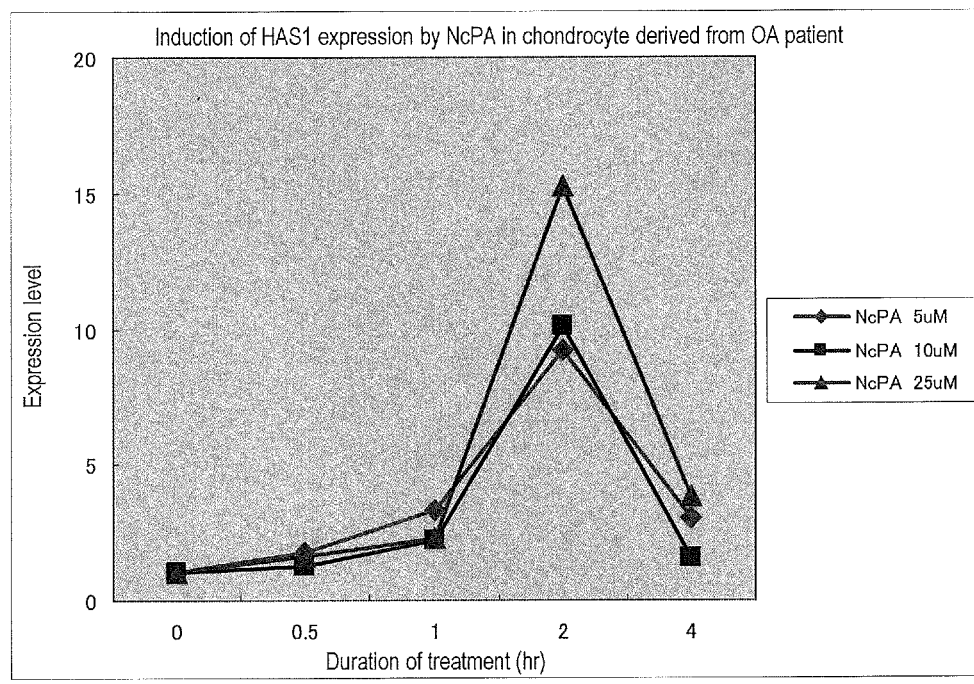
Figure 2:
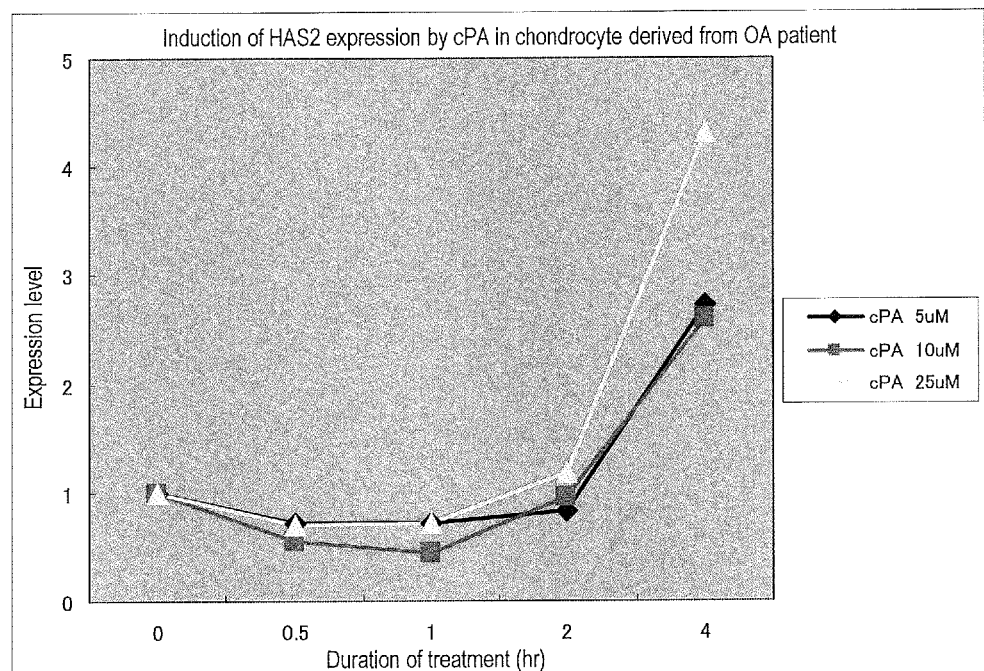
FIG. 2 shows the results of examination of effects of a cyclic phosphatidic acid derivative on expression of the hyaluronic acid synthase gene (HAS2) in chondrocytes derived from a patient with osteoarthritis.
Figure 2:
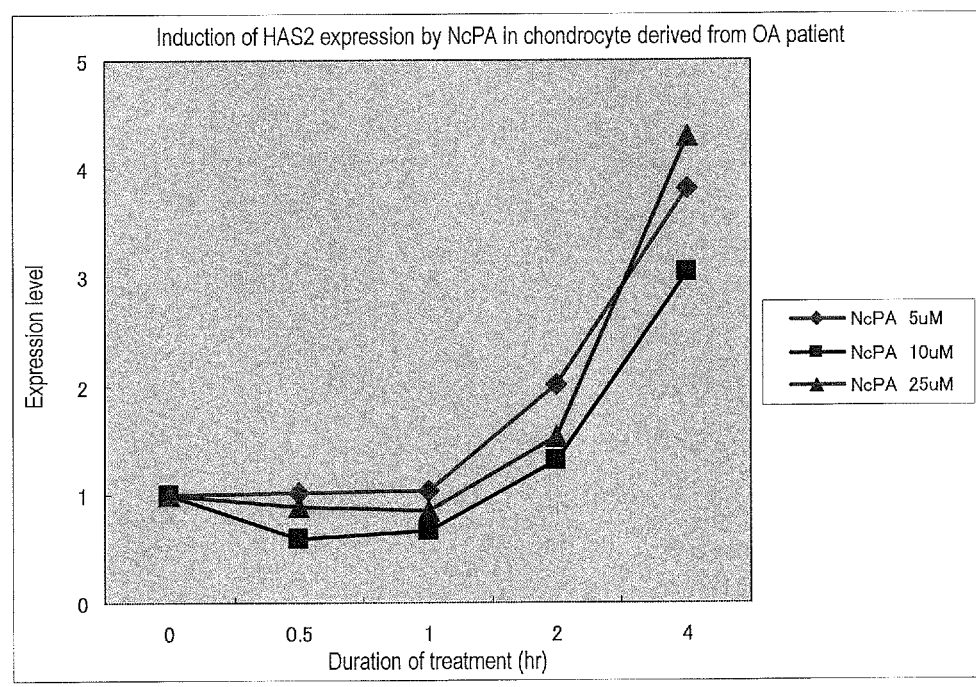
Figure 3:
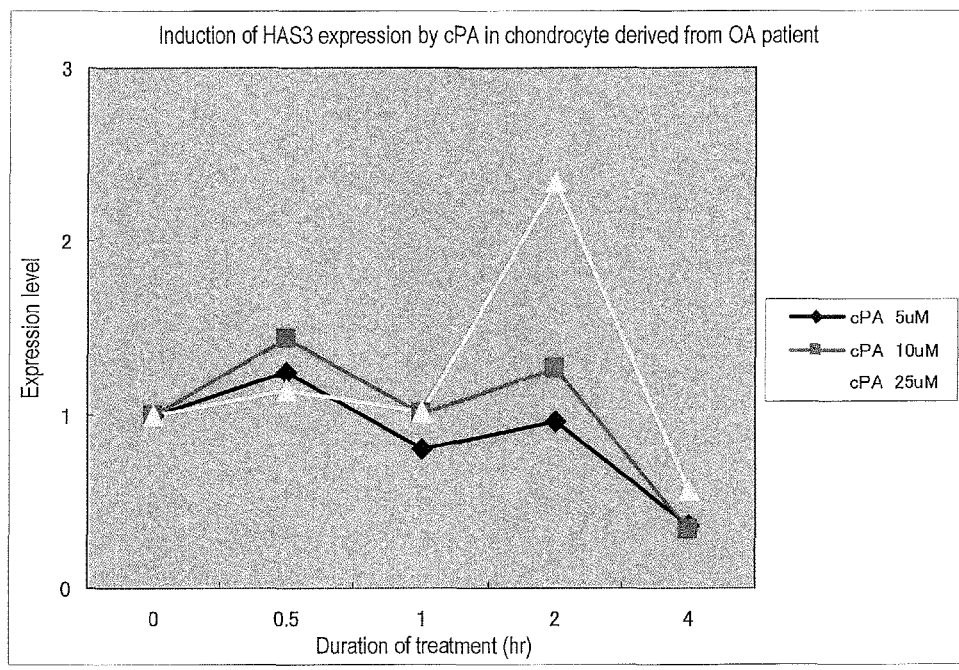
FIG. 3 shows the results of examination of effects of a cyclic phosphatidic acid derivative on expression of the hyaluronic acid synthase gene (HAS3) in chondrocytes derived from a patient with osteoarthritis.
Figure 3:
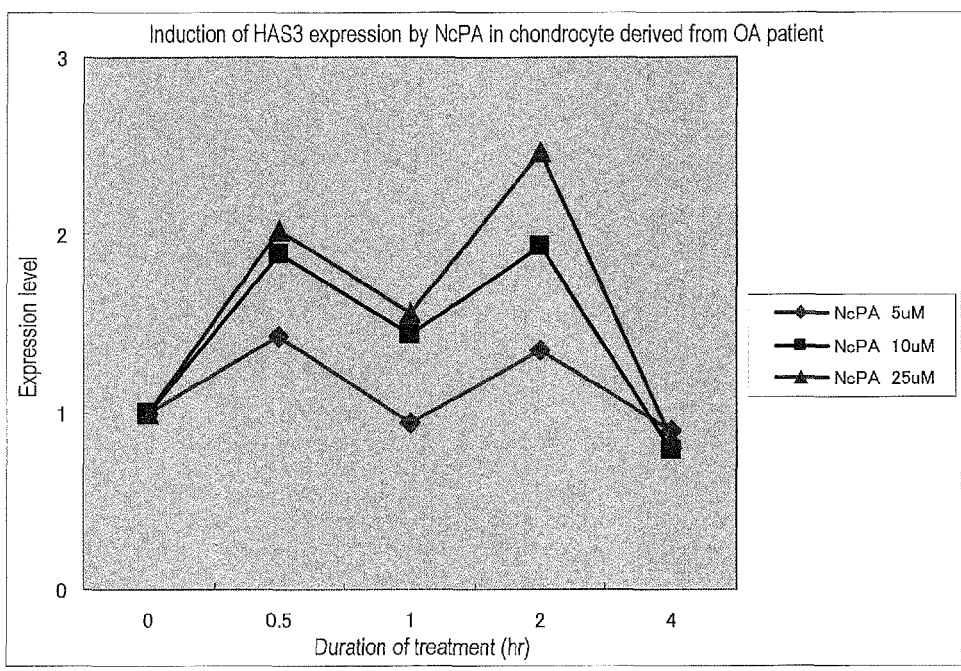
Figure 4:
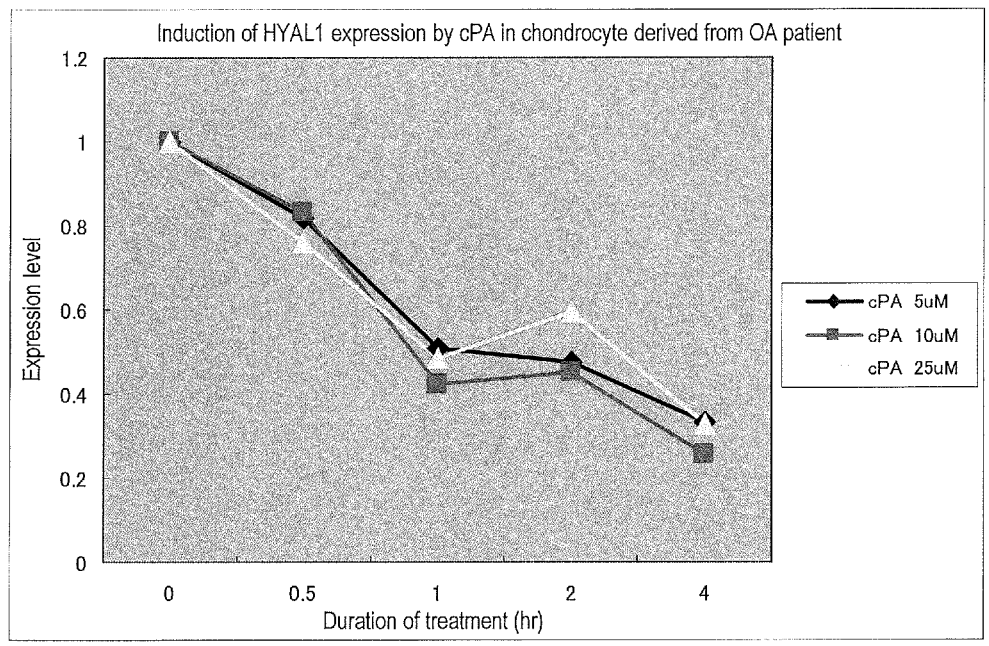
FIG. 4 shows the results of examination of effects of a cyclic phosphatidic acid derivative on expression of the hyaluronidase gene (HYAL1) in chondrocytes derived from a patient with osteoarthritis.
Figure 4:
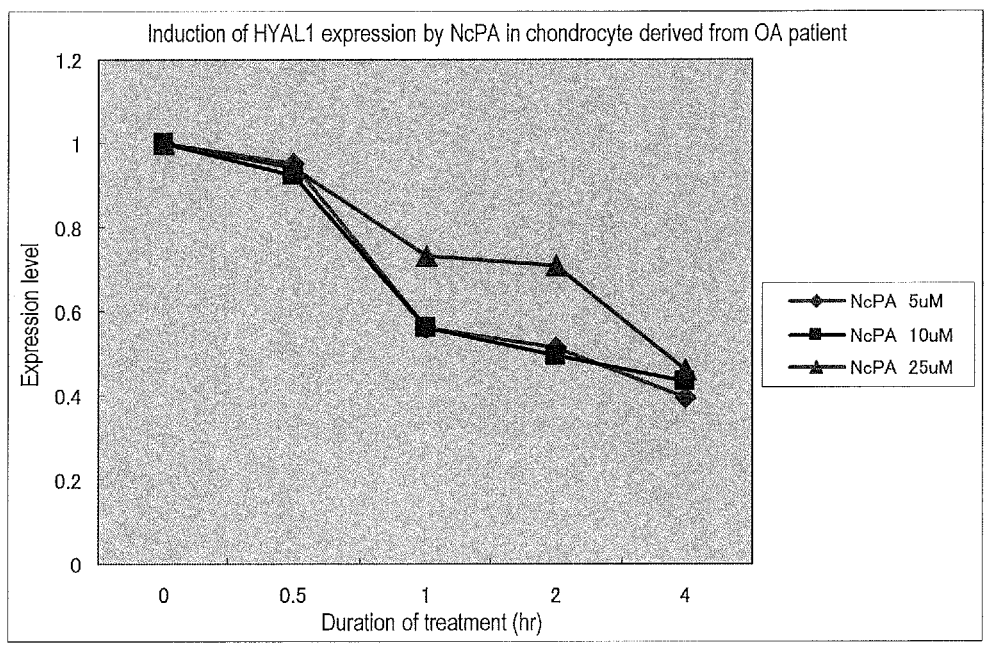
Figure 5:
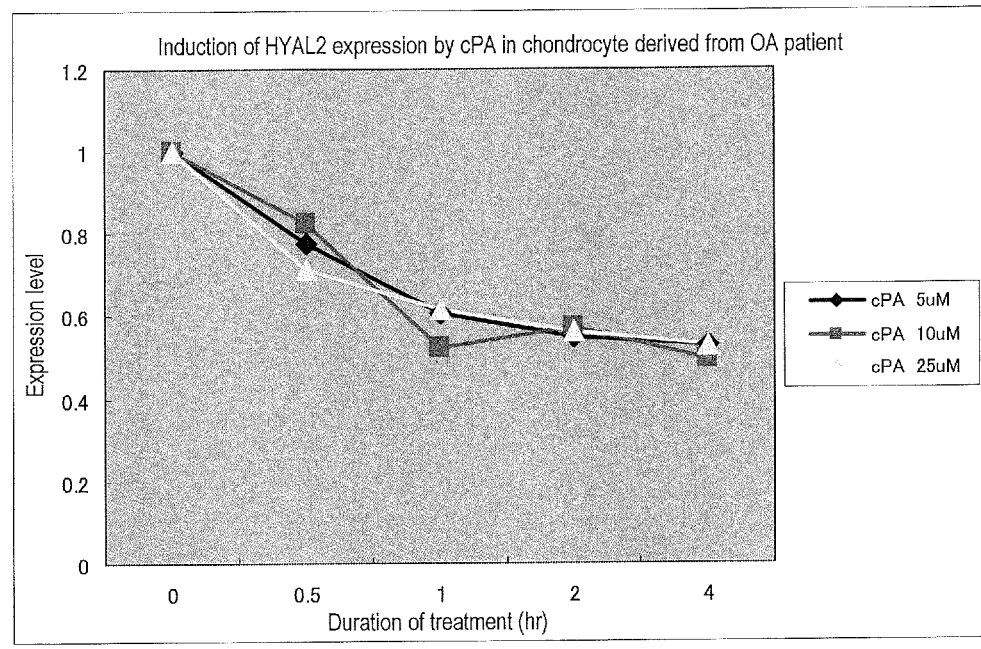
FIG. 5 shows the results of examination of effects of a cyclic phosphatidic acid derivative on expression of the hyaluronidase gene (HYAL2) in chondrocytes derived from a patient with osteoarthritis.
Figure 5:
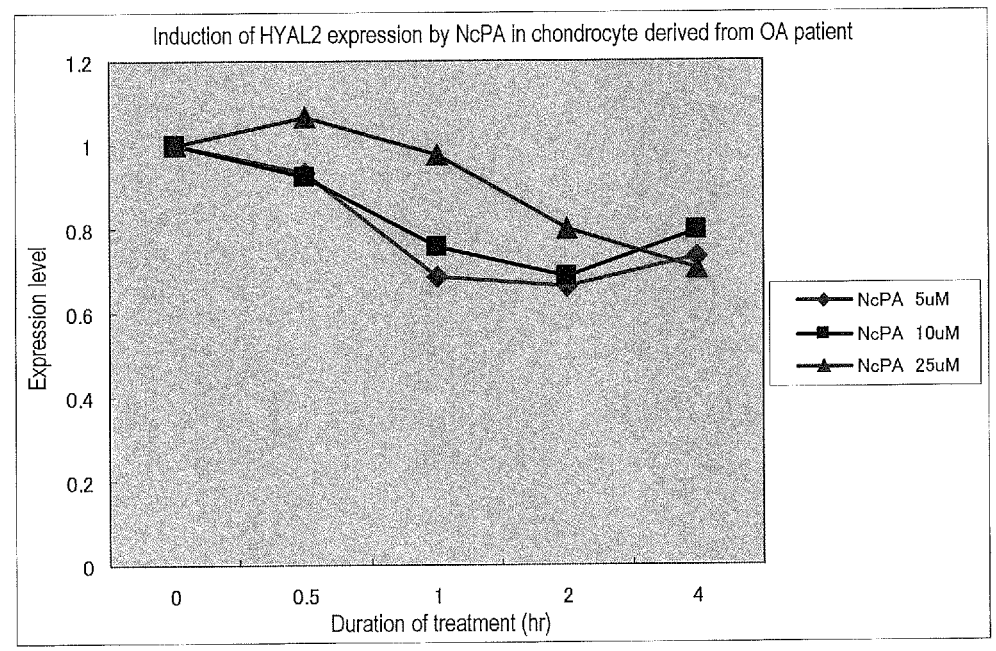

Hereafter, the present invention is described in greater detail.

The therapeutic agent for arthrosis according to the present invention can be used for treatment of arthrosis, such as osteoarthritis, articular rheumatism, and rheumatic fever (and osteoarthritis, in particular). Such agent comprises, as an active ingredient, cyclic phosphatidic acid, carbacyclic phosphatidic acid, or a salt thereof. Any compound can be used as cyclic phosphatidic acid, carbacyclic phosphatidic acid, or a salt thereof without particular limitation, provided that such compound exhibits the effects of the present invention. Preferable examples include compounds represented by formula (I) below:

[Formula 2]

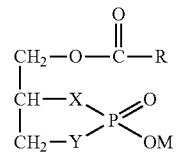

wherein R represents a linear or branched alkyl group having 1 to 30 carbon atoms, a linear or branched alkenyl group having 2 to 30 carbon atoms, or a linear or branched alkynyl group having 2 to 30 carbon atoms, which may contain a cycloalkane or aromatic ring; X and Y each independently represent an oxygen atom or a methylene group, provided that X and Y do not simultaneously represent a methylene group; and M represents a hydrogen atom or an alkali metal atom.

In Formula (I), specific examples of a linear or branched alkyl group having 1 to 30 carbon atoms represented by a substituent R include a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, and an eicosyl group.

Specific examples of linear or branched alkenyl groups having 2 to 30 carbon atoms represented by a substituent R include an allyl group, a butenyl group, an octenyl group, a decenyl group, a dodecadienyl group, and a hexadecatrienyl group. More specific examples thereof include an 8-decenyl group, an 8-undecenyl group, an 8-dodecenyl group, an 8-tridecenyl group, an 8-tetradecenyl group, an 8-pentadecenyl group, an 8-hexadecenyl group, an 8-heptadecenyl group, an 8-octadecenyl group, an 8-icocenyl group, an 8-docosenyl group, a heptadeca-8,11-dienyl group, a heptadeca-8,11,14-trienyl group, a nonadeca-4,7,10,13-tetrenyl group, a nonadeca-4,7,10,13,16-pentenyl group, and a henicosa-3,6,9,12,15,18-hexenyl group.

Specific examples of linear or branched alkynyl groups having 2 to 30 carbon atoms represented by a substituent R include an 8-decynyl group, an 8-undecynyl group, an 8-dodecynyl group, an 8-tridecynyl group, an 8-tetradecynyl group, an 8-pentadecynyl group, an 8-hexadecynyl group, an 8-heptadecynyl group, an 8-octadecynyl group, an 8-icocynyl group, an 8-dococynyl group, and a heptadeca-8,11-diynyl group.

Specific examples of the cycloalkane ring, which may be contained in the above-described alkyl, alkenyl, or alkynyl group, include a cyclopropane ring, a cyclobutane ring, a cyclopentane ring, a cyclohexane ring, and a cyclooctane ring. The cycloalkane ring may contain one or more hetero atoms, and examples thereof include an oxylane ring, an oxetane ring, a tetrahydrofuran ring, and an N-methylprolidine ring.

Specific examples of the aromatic ring, which may be contained in the above-described alkyl, alkenyl, or alkynyl group, include a benzene ring, a naphthalene ring, a pyridine ring, a furan ring, and a thiophene ring.

When the substituent R is an alkyl group substituted with a cycloalkane ring, accordingly, specific examples include a cyclopropylmethyl group, a cyclohexylethyl group, and an 8,9-methanopentadecyl group.

When the substituent R is an alkyl group substituted with an aromatic ring, specific examples include a benzyl group, a phenetyl group, and a p-pentylphenyloctyl group.

Preferably, R represents a linear or branched alkyl group having 9 to 17 carbon atoms, a linear or branched alkenyl group having 9 to 17 carbon atoms, or a linear or branched alkynyl group having 9 to 17 carbon atoms. More preferably, R represents a linear or branched alkyl group having 9, 11, 13, 15, or 17 carbon atoms or a linear or branched alkenyl group having 9, 11, 13, 15, or 17 carbon atoms. Particularly preferably, R represents a linear or branched alkenyl group having 9, 11, 13, 15, or 17 carbon atoms.

X and Y in the compound represented by Formula (I) each independently represent an oxygen atom (—O—) or a methylene group (—CH$_2$—), provided that X and Y do not simultaneously represent a methylene group. That is, combinations of X and Y include the following three patterns:

(1) X represents an oxygen atom and Y represents an oxygen atom;

(2) X represents an oxygen atom and Y represents a methylene group; or (3) X represents a methylene group and Y represents an oxygen atom.

M in the cyclic phosphatidic acid derivative represented by Formula (I) represents a hydrogen atom or an alkali metal atom Examples of alkali metal atoms include lithium, sodium and potassium, with sodium being particularly preferable.

Specifically, the compound represented by Formula (I) in the present invention is particularly preferably a cyclic phosphatidic acid or a carbacyclic phosphatidic acid derivative having, as an acryl group at position 1, an oleoyl group in which the substituent R represents an alkenyl group having 17 carbon atoms (abbreviated as "C18:1") or a palmitoleoyl group in which the substituent R represents an alkenyl group having 15 carbon atoms (abbreviated as "C16:1").

The compound represented by Formula (I) may comprise an isomer, such as a positional isomer, geometric isomer, tautomer, or optical isomer, in accordance with the type of a substituent thereof. All possible isomers and mixtures comprising two or more types of such isomers at a certain ratio are within the scope of the present invention.

In addition, the compound represented by Formula (I) may be in the form of an adduct composed of the compound and water or various types of solvents (hydrates or solvates). Such adduct is also within the scope of the present invention. Moreover, any crystal forms of the compound represented by Formula (I) and salts thereof are also within the scope of the present invention.

A compound represented by Formula (I) in which both X and Y represent oxygen atoms can be chemically synthesized in accordance with the method described in, for example, JP Patent Publication (Kokai) No. H05-230088 A (1993), H07-149772 A (1995), 1107-258278 A (1995), or 1109-25235 A (1997).

Also, a compound represented by Formula (I) in which both X and Y represent oxygen atoms can be synthesized in accordance with the method described in JP Patent Publication (Kokai) No. 2001-178489 A by allowing phospholipase D to react with lysophospholipid. Lysophospholipid used herein is not particularly limited, so long as it is capable of reacting with phospholipase D. Many types of lysophospholipids are known, molecular species having different types of fatty acids or having ether or vinyl ether bonds are known, and such lysophospholipids are commercially available. As phospholipase D, those derived from higher-order plants such as cabbage or peanuts or those derived from microorganisms such as *Streptomyces chromofuscus* or *Actinomadula* sp., are commercially available as reagents, although a cyclic phosphatidic acid is synthesized by an enzyme derived from the *Actinomadula* sp. No. 362 strain in a very selective manner (JP Patent Publication (Kokai) No. H11-367032 A (1999)). The reaction between lysophospholipid and phospholipase D may be carried out under any conditions, so long as an enzyme is able to exert its activity. For example, the reaction can be carried out in an acetate buffer containing calcium chloride (pH: about 5 to 6) at room temperature or higher (preferably 37° C.) for 1 to 5 hours. The resulting cyclic phosphatidic acid derivative can be purified in accordance with a conventional technique by means of, for example, extraction, column chromatography, or thin-layer chromatography (TLC).

A compound represented by Formula (I) in which X represents an oxygen atom and Y represents a methylene group can be synthesized in accordance with the method described in literature (Kobayashi, S. et al., Tetrahedron Letters, 34, 4047-4050, 1993) or WO 2002/094286. An example of a specific synthetic pathway is shown below.

[Formula 3]

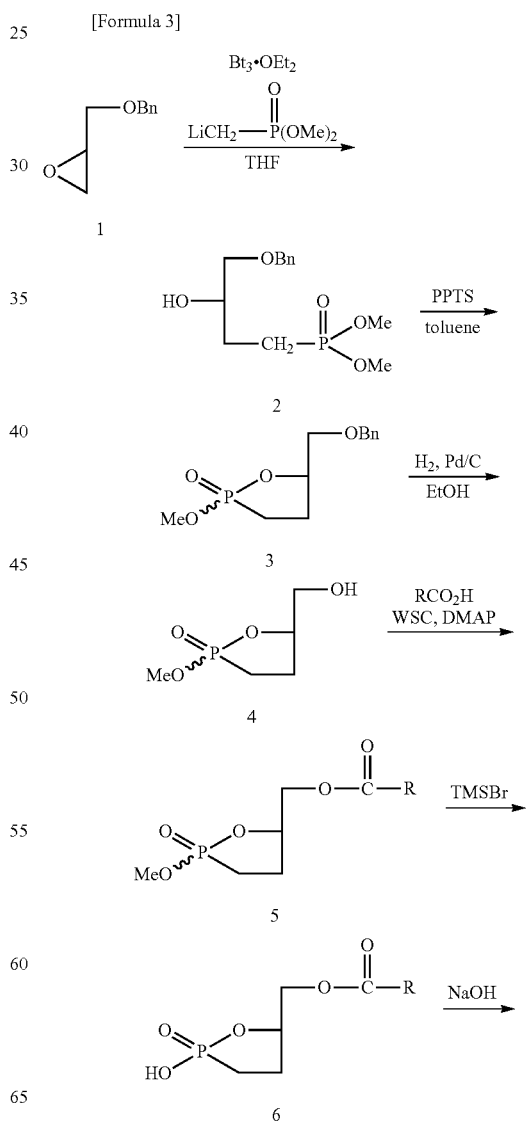

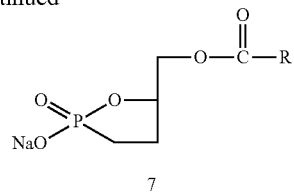

In the above formulae, at the outset, commercially available (R)-benzyl glycidyl ether (1) is activated with the aid of $BF_3 \cdot Et_2O$, n-BuLi is allowed to react with dimethyl methylphosphonate, and the resulting lithiated form is subjected to the reaction to obtain an alcohol (2).

The resulting alcohol is subjected to reaction in toluene with the use of an excessive amount of a pyridinium salt of p-toluenesulfonic acid at 80° C. to obtain a cyclized form (3). The resulting cyclized form is hydrolyzed under a hydrogen atmosphere with the use of 20% $Pd(OH)_2$—C to perform debenzylation (4). 1-Ethyl-3-(3-dimethylaminopropyl)carbodiimide hydrochloride, as a condenser, is allowed to react with a fatty acid to obtain a coupled form (5). Subsequently, bromotrimethylsilane is used as a nucleophile to exclusively remove a methyl group in a position-selective manner, thereby obtaining a cyclic phosphoric acid (6). The resultant is introduced into a separatory funnel with the aid of ether, and a small amount of an aqueous solution of 0.02 N sodium hydroxide is added dropwise thereto to separate liquids. The compound of interest is extracted and purified as a sodium salt (7).

A compound represented by Formula (1) in which X represents a methylene group and Y represents an oxygen atom can be synthesized in accordance with the method described in JP Patent Publication (Kokai) No. 2004-010582 A or International Publication WO 2003/104246.

The therapeutic agent for arthrosis according to the present invention is preferably provided in the form of a pharmaceutical composition that comprises one or more pharmaceutically acceptable additives and the compound represented by Formula (I) as an active ingredient.

The therapeutic agent for arthrosis according to the present invention can be administered in various forms, and administration may be carried out orally or parenterally (for example, intravenous, intramuscular, subcutaneous or intracutaneous injection, rectal administration, and permucosal administration may be employed). Examples of dosage forms for pharmaceutical compositions suitable for oral administration include a tablet, a granule, a capsule, a powder, a solution, a suspension, and syrup. Examples of dosage forms for pharmaceutical compositions suitable for parenteral administration include an injection, an infusion, a suppository, and a percutaneous absorption agent. The dosage form for the agent of the present invention is not limited thereto. Further, the agent can also be made into sustained-release formulations in accordance with methods known in the art.

Types of pharmaceutical additives used for producing the therapeutic agent for arthrosis according to the present invention are not particularly limited, and a person skilled in the art can select adequate additives. Examples of additives that can be used include an excipient, a disintegration agent or a disintegration auxiliary agent, a binder, a lubricant, a coating agent, a base, a dissolving agent or a solubilizer, a dispersant, a suspension agent, an emulsifier, a buffer, an antioxidant, an antiseptic, an isotonic agent, a pH adjusting agent, a dissolving agent, and a stabilizer. Each specific ingredient used for the above purposes is well known to a person skilled in the art.

Examples of pharmaceutical additives that can be used for the production of oral preparations include: an excipient, such as glucose, lactose, D-mannitol, starch, or crystalline cellulose; a disintegration agent or a disintegration auxiliary agent, such as carboxymethyl cellulose, starch, or carboxymethyl cellulose calcium; a binder, such as hydroxypropyl cellulose, hydroxypropyl methylcellulose, polyvinyl pyrrolidone, or gelatin; a lubricant, such as magnesium stearate or talc; a coating agent, such as hydroxypropyl methylcellulose, white sugar, polyethylene glycol, or titanium oxide; and a base, such as Vaseline, liquid paraffin, polyethylene glycol, gelatin, kaolin, glycerin, purified water, or hard fat.

Examples of the pharmaceutical additives that can be used for production of an injection or an infusion preparation include: a dissolving agent or a solubilizer that can be used for an aqueous injection or a use-time dissolution type injection, such as injection distilled water, physiological saline, propylene glycol, or a surfactant; an isotonic agent, such as glucose, sodium chloride, D-mannitol, or glycerin; and a pH adjusting agent, such as an inorganic acid, an organic acid, an inorganic base, or an organic base.

The therapeutic agent for arthrosis according to the present invention can be administered to mammals, including humans.

A dose of the therapeutic agent for arthrosis according to the present invention should be increased or decreased in accordance with conditions such as age, sex, body weight, symptoms of a patient, and the route of administration. The dose of the active ingredient per day per adult is generally 1 μg/kg to 1,000 mg/kg, and preferably 10 μg/kg to 100 mg/kg. The agent may be administered in the amounts mentioned above once a day or several separate times (for example, about 2-4 times) a day.

The present invention is described in greater detail with reference to the following examples, although the present invention is not limited to the examples.

Examples

Example 1

(1) Method (1-1) Culture of Articular Chondrocytes and Synoviocytes

Hyaline articular cartilage that was sampled from a patient with knee osteoarthrosis at the time of artificial knee joint replacement was used. Articular cartilage pieces were washed and subjected to enzyme treatment with pronase and collagenase to decompose cartilage matrices. Thereafter, cells were sampled, cultured, and then cryopreserved. Synoviocytes were also sampled. In this example, such articular chondrocytes and synoviocytes obtained from a patient with osteoarthritis were used, such cells were subjected to monolayer, high-density culture in order to avoid transformation, and the cultured cells were then subjected to the experiment. A medium composed of DMEM, 10% FBS, and 1% antibiotics/antifungus was used, the medium was replaced with a serum-free medium upon reaching confluence, and the experiment was then initiated.

(1-2) Addition of Cyclic Phosphatidic Acid or Carbacyclic Phosphatidic Acid (cPA)

As cyclic phosphatidic acid and carbacyclic phosphatidic acid, C16:1-cPA (cPA) and native cPA (NcPA) were used, respectively, and these substances were examined in terms of production of hyaluronic acid (HA), expression of hyaluronic acid (HA)-synthetic enzymes (HAS1, HAS2, and HAS3), and hyaluronic acid (HA)-degrading enzymes (HYAL1 and HYAL2) at concentrations of 0 to 50 nM for 0 to 48 hours.

The chemical structure of C16:1-cPA (indicated as "cPA" in the figure) is as shown below.

[Formula 4]

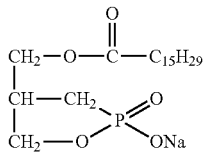

Native cPA (indicated as "NcPA" in the figure) was prepared in the manner described below (see Examples 1 and 3 of JP Patent Application No. 2011-126901).

Soybean phospholipid (10 g; lecithin content: 70%) was dissolved in 100 ml of 1 M acetate buffer (pH 6.5) containing 0.3 M calcium chloride, 6,000 units of *Streptomyces*-derived phospholipase A2 were added, and the mixture was subjected to reaction at 40° C. for 18 hours with stirring. The pH level of the reaction solution was adjusted to 2.5 to inactivate the enzyme, 100 ml of chloroform and 50 ml of methanol were added and thoroughly mixed via stirring, and lipid components were extracted. The chloroform layer was sampled and solidified to dryness under reduced pressure in a rotary evaporator. Acetone (100 ml) was added to the solid component to precipitate phospholipids, and free fatty acids were removed. The precipitate (5 g) was dissolved in 40 ml of chloroform, 10 ml of 1 M acetate buffer (pH 5.5) was added thereto, 1,500 units of *Actinomadura*-derived phospholipase D were further added, and the mixture was subjected to reaction at 40° C. for 18 hours with stirring. To the reaction solution, 20 ml of 3 M sodium chloride and 20 ml of 0.1 M EDTA solution were added, and the resultant was subjected to stirring at 40° C. for 1 hour. Further, 20 ml of methanol was added thereto, the mixture was thoroughly stirred, and the resultant was centrifuged at 3,000 rpm for 5 minutes to collect the chloroform layer. The solution was solidified to dryness under reduced pressure in a rotary evaporator and 3.8 g of sodium salt of cyclic phosphatidic acid was obtained. The yield was 54.3% since 3.8 g of cyclic phosphatidic acid Na was obtained from soybean phospholipid with lecithin content of 70% (i.e., 7 g of lecithin in 10 g of soybean phospholipid). Purity of a sodium salt of cyclic phosphatidic acid was analyzed using a silica gel plate, the sample was spread on the plate with chloroform:methanol:acetic acid:5% sodium disulfite (100: 40:12:5, V/V), and the plate was soaked in a mixture of 5% copper acetate, 8% phosphoric acid, and 2% sulfuric acid for a short period of time. The plate was air dried and heated at 180° C. for about 10 minutes, and the formed spots were inspected using a scanner (manufactured by ATTO Corporation). Specifically, a reference product (purity: 97%) was used as a control sample, and spots in the thin-layer chromatograph were examined using a densitometer, followed by quantification based on the area ratio. The purity of the sodium salt of cyclic phosphatidic acid in the product obtained in the above step was 54%.

The sodium salt of cyclic phosphatidic acid (500 mg) was dissolved in 5 ml of chloroform containing 10% methanol, applied to a silica gel column, spread with the aid of the solvent described above, further spread with the aid of chloroform containing 20% methanol, and fractionated to fractions of 10 ml each. Fractions containing sodium salt of cyclic phosphatidic acid were collected in accordance with the TLC method described above and solidified to dryness under reduced pressure in a rotary evaporator. Thus, 320 mg of sodium salt of cyclic phosphatidic acid powder was obtained. The purity of the sodium salt of cyclic phosphatidic acid in the sample was 95%.

(1-3) Measurement of HA-synthetic Enzyme Expression and HA-degrading Enzyme Expression A chondrocyte culture was replaced with a serum-free medium 24 hours before the initiation of the experiment, and cPA or N-cPA at various concentrations (0, 5, 10, 25, or 50 µM) was added. Also, a periosteal cell culture was replaced with a serum-free medium 24 hours before the initiation of the experiment, and cPA at various concentrations (0, 10, or 25 µM) was added. Total RNA was isolated from the cell culture 0, 0.5, 1, 2, and 4 hours later, cDNA was synthesized, and HAS1, HAS2, HAS3, HYL1, and HYL2 expression levels were quantified by real-time PCR. The expression level was determined relative to the β actin gene (i.e., the control gene) and it was represented relative to the control value without the addition of cPA or N-cPA or the value before addition thereof, which was normalized to 1.

Specifically, the expression ratio was determined by the ΔΔCt method comprising comparing the differences in cycle number threshold (Ct value) obtained for the target and the control in a sample with the CT-value obtained for a control sample, as described below.

1) ΔCt is determined using Ct obtained for a relevant sample:

$\Delta Ct = Ct \text{ (target gene)} - Ct \text{ (control gene)}$

2) ΔΔCt is determined:

$\Delta\Delta Ct = \Delta Ct \text{ (target sample)} - \Delta Ct \text{ (control sample)}$ 3) Target gene expression level in the target sample is normalized:

$2^{(-\Delta\Delta Ct)}$

4) Changes in target gene expression levels are determined with reference to the control sample value normalized to 1.

(1-4) Measurement of Hyaluronic Acid (HA) Production

A chondrocyte culture was replaced with a serum-free medium 48 hours before the initiation of the experiment, and cPA and N-cPA at various concentrations (0, 10, or 50 M) was added. A culture supernatant was sampled 0, 6, 12, 24, and 48 hours later. By the sandwich ELISA method involving the use of HA-binding proteins derived from bovine nasal cartilage (QnE Hyaluronic Acid (HA) ELISA Assay kit; Biotech Trading Partners, Inc), HA production was quantified.

Figure 7:
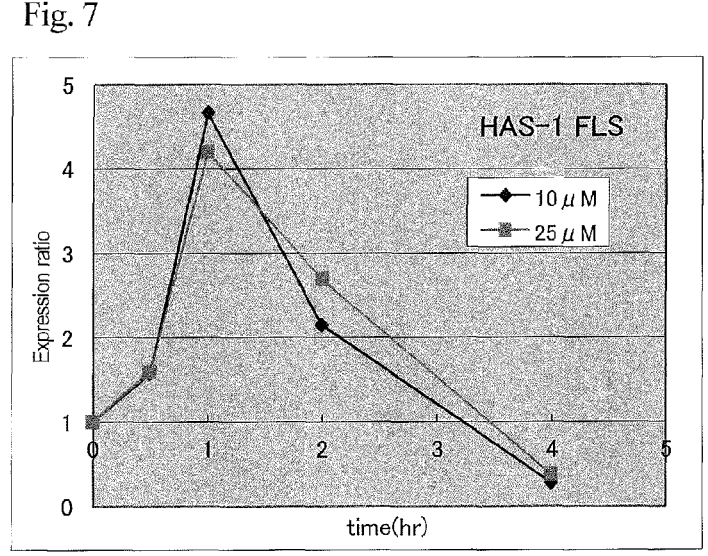
FIG. 7 shows the results of examination of effects of a cyclic phosphatidic acid derivative (test compound: ScPA) on expression of the hyaluronic acid synthase genes (HAS1, HAS2, and HAS3) in synoviocytes derived from a patient with osteoarthritis.
Figure 7:
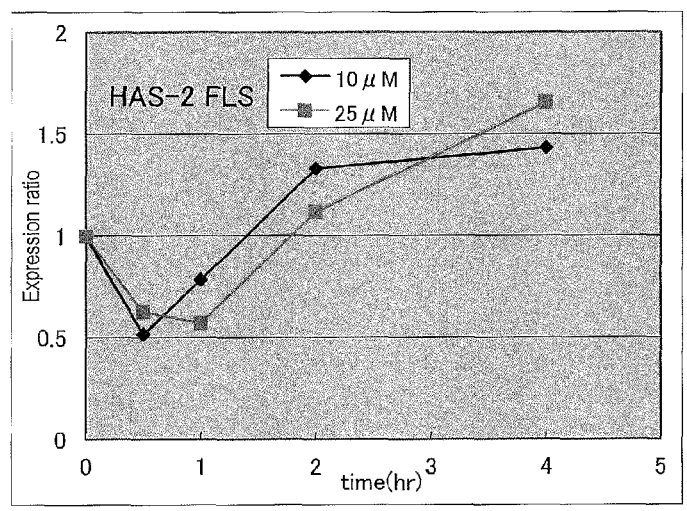
Figure 7:
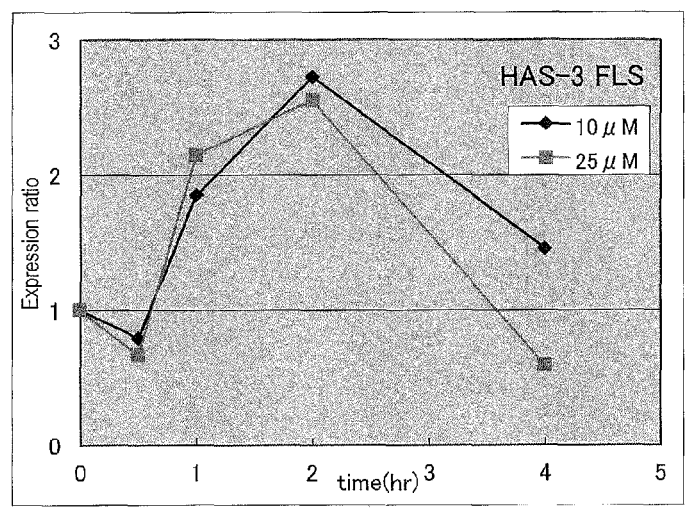
Figure 8:
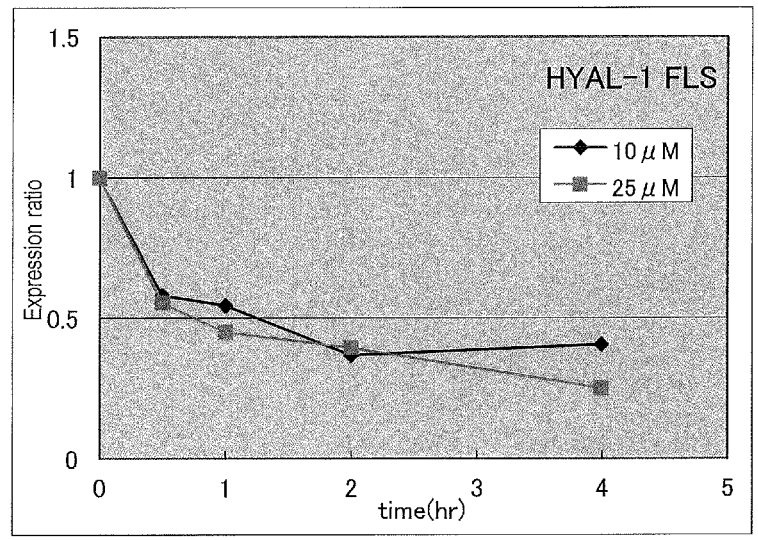
FIG. 8 shows the results of examination of effects of a cyclic phosphatidic acid derivative on expression of the hyaluronidase genes (HYAL1 and HYAL2) in synoviocytes derived from a patient with osteoarthritis.
Figure 8:
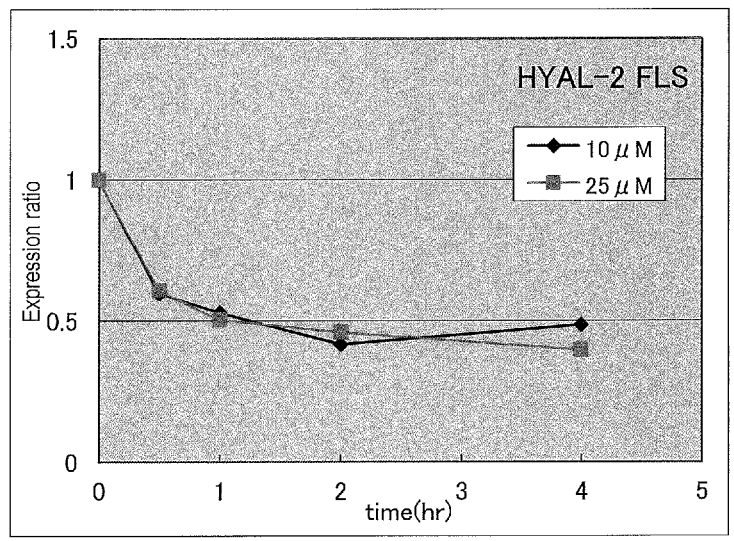

(2) Results (2-1) Results of Expression Assay of HA-Synthetic Enzymes and HA-Degrading Enzymes FIG. 1 to FIG. 5 each show the results of expression assay of HA-synthetic enzymes and HA-degrading enzymes in chondrocytes. As shown in FIG. 1 to FIG. 5, C16:1-cPA (cPA) continuously induced HAS2 expression in a concentration-dependent manner. While HAS1 and HAS3 expression was transiently induced 2 hours after the addition, the expression level was lowered 4 hours later. NcPA produced similar results. The expression of HA-degrading enzymes (HYL1, HYL2, and HYL3) was not influenced. Such results demonstrate that cPA and NcPA induce expression of HA-synthetic enzymes. Also, FIG. 7 shows the results of expression assay of HA-synthetic enzymes in synoviocytes and FIG. 8 shows the results of expression assay of HA-degrading enzyme in synoviocytes.

(2-2) Results of Measurement of Hyaluronic Acid (HA) Production

Figure 6:
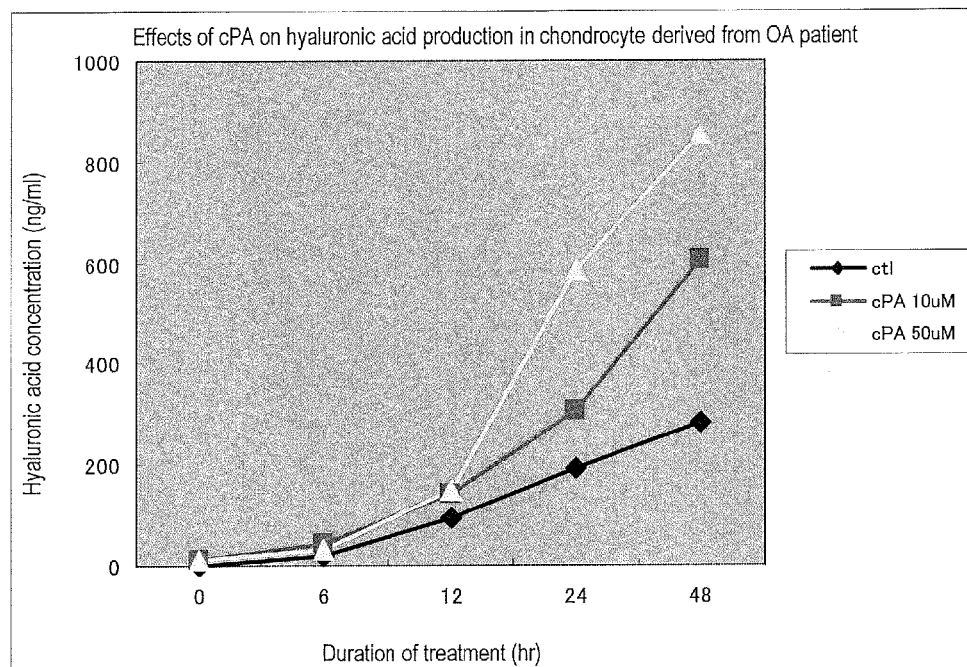
FIG. 6 shows the results of examination of effects of a cyclic phosphatidic acid derivative on hyaluronic acid production in chondrocytes derived from a patient with osteoarthritis.
Figure 6:
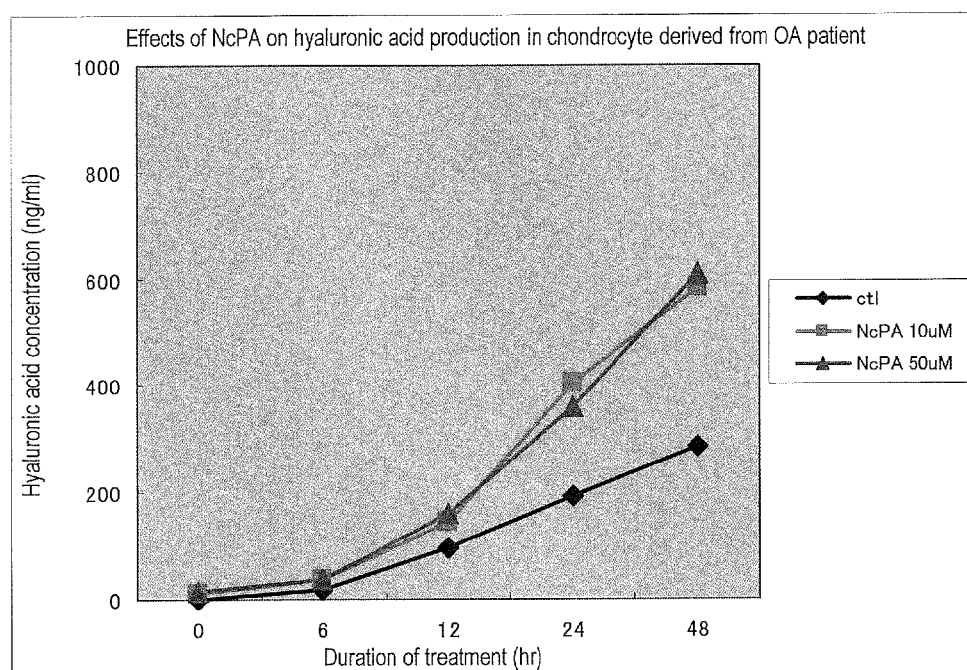

FIG. 6 shows the results of measurement of HA production. As shown in FIG. 6, C16:1-cPA (cPA) accelerated the HA synthesis in chondrocytes with the elapse of time and released HA to the outside of the cells. Forty eight hours later, the amount of HA produced in the group to which cPA had been added at 50 nM was approximately 3 times greater than that produced in the the vehicle administered group. NcPA produced similar results. Such results demonstrate that C16:1-cPA (cPA) and NcPA accelerate HA production in articular chondrocytes with osteoarthritis (OA).

(3) Conclusions

The cyclic phosphatidic acid or carbacyclic phosphatidic acid represented by Fat nula (I) was found to induce expression of HA-synthetic enzymes and to accelerate production of HA in articular chondrocytes of humans with OA, as with the case of dermal fibroblasts.

Example 2

Evaluation of Effects of ScPA on Osteoarthritis in Rabbit Knee (1) Method (1-1) Animals Used and Rearing Conditions Twelve 11- to 12-week-old male rabbits (Kbs:NZW) were used. Rabbits were reared in separate cages (one rabbit per cage) at 14.4° C. to 24.9° C. under light (12 hours from 7:00 am to 7:00 pm) with continuous ventilation. Rabbits were allowed to eat 150 g of feed (CR-3, CLEA Japan, Inc.) per day and to drink tap water.

(1-2) Substances to be Administered (9Z)-9-Octadecenoic acid-(2-hydroxy-2-oxide-1,2-oxaphospholan-4-yl)methyl ester sodium salt (C18:1-cPA; hereafter, referred to as "ScPA") was used.

[Formula 5]

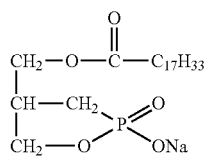

Physiological saline was used as a vehicle.

(1-3) Preparation of Osteoarthritis Model

Hair in the vicinity of the knee joint of the right hind limb of a rabbit was shaved using electrical clippers under deep anesthesia, and the shaved area was disinfected with Isodine. The outer coat on the medial aspect of the right hind limb was incised with a surgical knife, the boundary between the medial aspect and the articular capsule of the patellofemoral ligament was further incised, and the medial patellofemoral ligament was then dissected. Thereafter, the articular capsule was spread wide open to expose the medial meniscus, which was then completely removed. Following the removal of the meniscus, tissue and epidermis in the vicinity of the articular capsule were sutured. At the time of suturing, the site of operation was washed with physiological saline (titer: 500 mg/20 ml) containing antibiotics (Viccillin, Meiji Seika Pharma Co., Ltd.).

On the day of surgical treatment (day 0), rabbits were allowed to freely drink water under fasting conditions. Awakening was confirmed upon observation of spontaneous movement of heads. In order to prevent the animals from losing body temperature, the animals were kept warm by wrapping their trunks with towels until awakening had been confirmed. Also, body positions were adequately changed in order to prevent blood from pooling. For the purpose of infection control, an antibiotic (Viccillin: 3 units/kg) was intramuscularly administered once a day up to 5 days after the treatment (day 5).

After the model animals were prepared, they were divided into two groups each consisting of 6 individuals while averaging body temperature (i.e., the vehicle administered group of Animal Numbers 101 to 106 and the test substance (ScPA) administered group of Animal Numbers 201 to 206).

(1-4) Administration of Test Compound and Vehicle into Joint Cavity

The test compound and the vehicle were administered in the manner described below.
  Route of administration: into the joint cavity
  Site of administration: right hind limb (treated limb)
  Timing of administration: on days 7, 11, 14, 18, 21, 25, 28, 32, 35, and 39
  Dosage: Test compound: 10 µg/rabbit (volume: 0.2 ml)
  Vehicle: 0.2 ml/rabbit
  Means of administration: with the use of a 1.0-ml syringe (Terumo Corporation) and a 27 G injection needle (Terumo Corporation)

(1-5) Pain Assessment (Weight Distribution Across both Hind Limbs)

Frequency of Measurement:

Measurement was carried out seven times in total: i.e., before treatment and 1, 2, 3, 4, 5, and 6 weeks after the treatment.

Method of Measurement:

Body weights loaded on the right hind limb and the left hind limb were separately measured using a weight scale, and the weight distribution on the treated limb (the right hind limb) was determined using the following equation.

Weight distribution (%) on treated limb (right hind limb)=[right hind limb (kg)/(right hind limb (kg)+left hind limb (kg))]×100

(1-6) Swelling Assessment (Articular Swelling of both Hind Limbs)

Frequency of Measurement:

Measurement was carried out 6 weeks after the treatment.

Method of Measurement:

The widest areas at the joints of the right and left hind limbs were measured using digital calipers, and the articular swelling induced by osteoarthritis was determined using the following equation.

Swelling (%) of treated limb (right hind limb)=[(right hind limb (mm)−left hind limb (mm))/(left hind limb (mm)+left hind limb (mm))]×100

(1-7) Sampling of Biomaterials (day 42) and Post-Sampling Treatment

Four limbs were dissected from the animals under deep anesthesia, causing them to bleed to death. Thereafter, the femur condyle and the tibial condyle were removed from the knee joint of the treated limb (the right hind limb), followed by fixation in a 10% neutral buffered formalin solution.

(1-8) Preparation of Pathological Specimens and Histopathological Evaluation Thereof The femur and the tibia that had been soaked and fixed in a 10% neutral buffered formalin solution were subjected to demineralization with EDTA. After the completion of demineralization, the colored sites identified below were embedded in paraffin in accordance with a conventional technique, and the resultant was sliced to a thickness of 4 μm each. The slices were subjected to hematoxylin-eosin (HE) staining and safranin O (proteoglycan) staining and histopathologically examined under an optical microscope (BX51TF; OLYMPUS). The degree of cartilage degeneration of the pathological specimens was evaluated in accordance with the criteria shown in Table 1 below (Kikuchi, T, Yoneda, H. et al., Osteoarthritis cartilage, 4; p. 99 and continuing pages, 1996). Specifically, the specimens were evaluated in terms of loss of the following 8 items according to a five-grade evaluation (0 to +4): superficial layer; cartilage erosion; fibrillation and/or fissure; lowered proteoglycan stainability (safranin O stainability); disorganization of chondrocytes; loss of chondrocytes; exposure of subchondral bone; and cluster formation. The sum total score of all items was defined as the overall score. Observation items without specific criteria defined in Table 1 were evaluated in accordance with the criteria shown in Table 2 below (Naoki Ishiguro et al., Journal of Surgery, 29: p. 112 and continuing pages, 2010).

TABLE 1

| Observation | Score | | | |
|---|---|---|---|---|
| | 1 | 2 | 3 | 4 |
| Loss of superficial layer | <sight | Moderate | Focally severe | Extensive severe |
| Erosion of cartilage | <Detectable | Moderate | Focally severe | Extensive severe |
| Fibrillation and/or fissures | <Noticeable (<1very mall) | Moderate (1 small) | Marked (2 small or 1 medium) | Extensive (3 small, 2 medium or 1 |
| Loss of proteoglycan | <Paler stain than control | Moderate loss of safraniophilia | Marked loss of safraniophilia | Total loss of safraniophilia |
| Disorganization of chondrocyte | Noticeable | Moderate, with | Marked loss of | No recognizable |
| Loss of chondrocyte | <Noticeable Decrease in cells | Moderate decrease in cells | Marked decrease in cells | Very extensive decrease in cells |
| Exposure of subchondral bone | <Focal Exposure of bone | Moderate Exposure of bone | Fairly extensive exposure of bone | Very extensive exposure of bone |
| Cluster formation [a] | <3-4 small, or 1-2 | 5-6 small, 3-4 | 7 or more small, 5- | 7 or more medium |

[a] Small; 2-4 cells, Medium: 5-8 cells, Large: 9 or more cells

TABLE 2

| Observation | Score | Criteria |
|---|---|---|
| Cartilage erosion | 0 | No change |
| | 1 | Lesions limited to the superficial to intermediate layers are observed throughout 1/3 or less of the area of the evaluation site in the width direction |
| | 2 | Lesions limited to the superficial to intermediate layers are observed throughout 1/3 to 2/3 of the area or lesions reaching the deep layer are observed throughout 1/3 or less of the area of the evaluation site in the width direction |
| | 3 | Lesions limited to the superficial to intermediate layers are observed throughout 2/3 or more of the area or lesions reaching the deep layer are observed throughout 1/3 to 2/3 of the area |
| | 4 | Lesions limited to the superficial to intermediate layers are observed throughout the entire area or lesions reaching the deep layer are observed throughout 2/3 or more of the area |
| Fibrillation/ fissure | 0 | No change |
| | 1 | Lesions limited to the superficial to intermediate layers are observed throughout 1/3 or less of the area of the evaluation site in the width direction |
| | 2 | Lesions limited to the superficial to intermediate layers are observed throughout 1/3 to 2/3 of the area or lesions reaching the deep layer are observed throughout 1/3 or less of the area of the evaluation site in the width direction |
| | 3 | Lesions limited to the superficial to intermediate layers are observed throughout 2/3 or more of the area or lesions reaching the deep layer are observed throughout 1/3 to 2/3 of the area |
| | 4 | Lesions limited to the superficial to intermediate layers are observed throughout the entire area or lesions reaching the deep layer are observed throughout 2/3 or more of the area |
| Loss of superficial layer | 0 | No change |
| | 1 | Lesions account for 1/4 or less of the area of the evaluation site |
| | 2 | Lesions account for 1/4 to 2/4 of the area of the evaluation site |
| | 3 | Lesions account for 2/4 to 3/4 of the area of the evaluation site |
| | 4 | Lesions account for 3/4 or more of the area of the evaluation site |
| Lowered proteoglycan stainability | 0 | No change |
| | 1 | Lesions account for 1/4 or less of the area of the evaluation site |
| | 2 | Lesions account for 1/4 to 2/4 of the area of the evaluation site |
| | 3 | Lesions account for 2/4 to 3/4 of the area of the evaluation site |
| | 4 | Lesions account for 3/4 or more of the area of the evaluation site |
| Disorganization of chondrocytes | 0 | No change |
| | 1 | Lesions account for 1/4 or less of the area of the evaluation site |
| | 2 | Lesions account for 1/4 to 2/4 of the area of the evaluation site |
| | 3 | Lesions account for 2/4 to 3/4 of the area of the evaluation site |
| | 4 | Lesions account for 3/4 or more of the area of the evaluation site |
| Loss of chondrocytes | 0 | No change |
| | 1 | Lesions account for 1/8 or less of the area of the evaluation site |
| | 2 | Lesions account for 1/8 to 1/3 of the area of the evaluation site |
| | 3 | Lesions account for 1/3 to 2/3 of the area of the evaluation site |
| | 4 | Lesions account for 2/3 or more of the area of the evaluation site |
| Exposure of subchondral bone | 0 | No change |
| | 1 | Lesions account for 1/8 or less of the area of the evaluation site |
| | 2 | Lesions account for 1/8 to 1/3 of the area of the evaluation site |
| | 3 | Lesions account for 1/3 to 2/3 of the area of the evaluation site |

TABLE 2-continued

| Observation | Score | Criteria |
|---|---|---|
| | 4 | Lesions account for ⅔ or more of the area of the evaluation site |
| Cluster formation | 0 | No change |
| | 1 | Lesions account for ⅛ or less of the area of the evaluation site |
| | 2 | Lesions account for ⅛ to ⅓ of the area of the evaluation site |
| | 3 | Lesions account for ⅓ to ⅔ of the area of the evaluation site |
| | 4 | Lesions account for ⅔ or more of the area of the evaluation site |

(1-9) Data Processing and Statistical Analysis

A group mean (mean) and its standard error (SE) for the weight distribution across both hind limbs and for articular swelling of both hind limbs were separately determined. Thereafter, the test substance administered group and the vehicle administered group were subjected to the F-test. When there was no variance between the samples, the Student's t-test was carried out. When there was variance between the samples, the Aspin-Welch t-test was carried out. Concerning the overall scores of the evaluation items of the histopathological test, the group mean (mean) and its standard error (SE) were determined, and the difference between the mean values for the two groups was then determined by the Mann-Whitney U test. The two-sided significance levels were set at 5% and 1%.

(2) Results (2-1) Pain Assessment (Weight Distribution Across both Hind Limbs)

Figure 9:
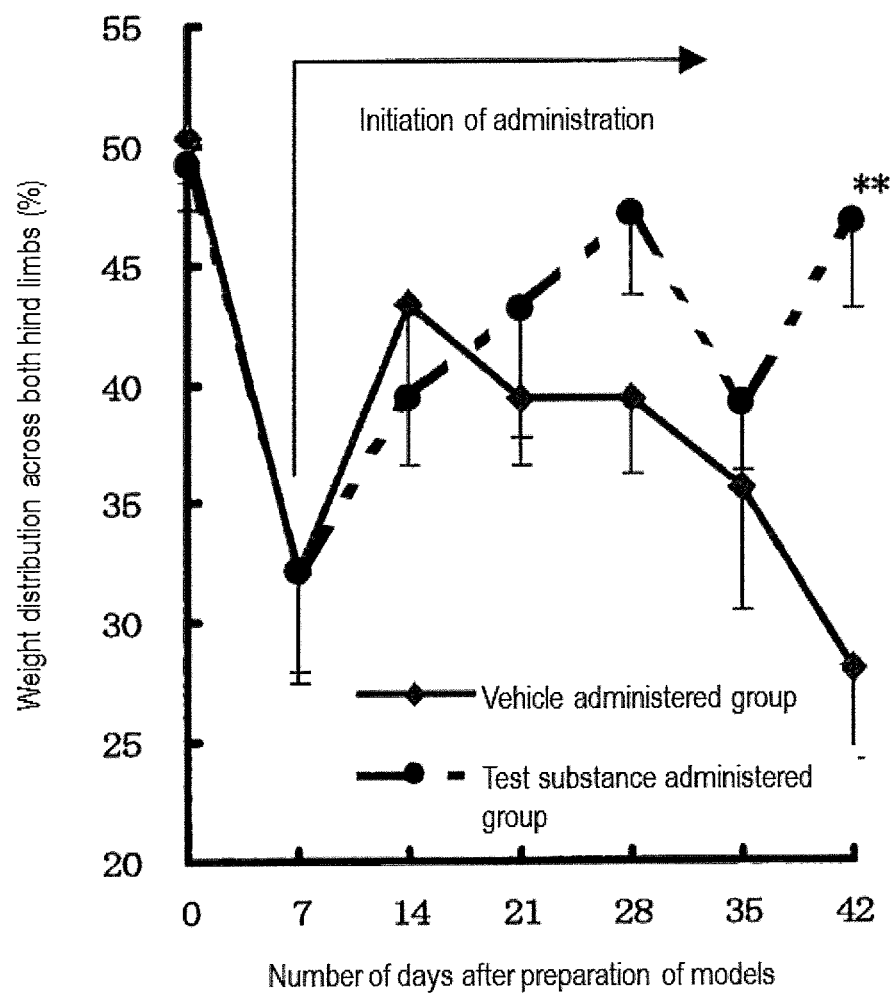
FIG. 9 shows changes in pain assessment (weight distribution across both hind limbs). Mean±standard error, n=6; in comparison with the group 1 (the vehicle administered group) *,**; significance levels at p<0.05 and p<0.01 (the Student's t test and the Aspin-Welch t test).

Table 3 and FIG. 9 show changes in weight distribution across both hind limbs from the day on which model animals were prepared (day 0) to the day on which biomaterials were sampled (day 42). In the vehicle administered group, recovery from surgical invasion was observed up to day 14, osteoarthritis was induced thereafter, the weight loaded on the treated limb (the right hind limb) was decreased because of the pain caused by osteoarthritis, and such weight was decreased to as low as 28.0% on the day on which biomaterials were sampled (day 42). In the test substance administered group, in contrast, recovery from surgical invasion was observed up to day 14, as with the vehicle administered group, and, thereafter, the weight loaded on the treated limb (the right hind limb) was maintained at higher levels up to the day on which biomaterials were sampled (day 42), compared with the vehicle administered group. A significant difference was observed as a result of measurement on day 42 (p=0.0053).

TABLE 3

Pain assessment (weight distribution across both hind limbs)

| Group | Animal No. | Item | Day 0 | Day 7 | Day 14 | Day 21 | Day 28 | Day 35 | Day 42 |
|---|---|---|---|---|---|---|---|---|---|
| Vehicle administered-group | 101 | Right hind limb (g) | 630 | 350 | 550 | 290 | 450 | 440 | 340 |
| | | Left hind limb (g) | 500 | 390 | 700 | 750 | 650 | 650 | 910 |
| | | Weight distribution (%) | 56 | 47 | 44 | 28 | 41 | 40 | 27 |
| | 102 | Right hind limb (g) | 550 | 240 | 160 | 320 | 100 | 130 | 80 |
| | | Left hind limb (g) | 500 | 500 | 160 | 320 | 300 | 800 | 550 |
| | | Weight distribution (%) | 52 | 32 | 50 | 50 | 25 | 14 | 13 |
| | 103 | Right hind limb (g) | 470 | 420 | 370 | 490 | 520 | 300 | 470 |
| | | Left hind limb (g) | 510 | 700 | 670 | 740 | 720 | 580 | 720 |
| | | Weight distribution (%) | 48 | 38 | 36 | 40 | 42 | 34 | 39 |
| | 104 | Right hind limb (g) | 390 | 300 | 200 | 380 | 480 | 510 | 290 |
| | | Left hind limb (g) | 450 | 640 | 500 | 600 | 550 | 750 | 930 |
| | | Weight distribution (%) | 46 | 32 | 29 | 39 | 47 | 40 | 24 |
| | 105 | Right hind limb (g) | 540 | 270 | 600 | 410 | 290 | 370 | 370 |
| | | Left hind limb (g) | 460 | 610 | 500 | 610 | 480 | 350 | 870 |
| | | Weight distribution (%) | 54 | 31 | 55 | 40 | 38 | 51 | 30 |
| | 106 | Right hind limb (g) | 380 | 50 | 450 | 450 | 590 | 380 | 490 |
| | | Left hind limb (g) | 460 | 340 | 500 | 680 | 740 | 760 | 900 |
| | | Weight distribution (%) | 45 | 13 | 47 | 40 | 44 | 33 | 35 |
| | | Mean | 50.3 | 32.1 | 43.3 | 39.4 | 39.4 | 35.6 | 28.0 |
| | | SE | 1.77 | 4.60 | 3.94 | 2.87 | 3.14 | 5.07 | 3.83 |
| Test substance Administered-group | 201 | Right hind limb (g) | 660 | 660 | 520 | 380 | 600 | 350 | 440 |
| | | Left hind limb (g) | 610 | 1010 | 770 | 710 | 700 | 650 | 620 |
| | | Weight distribution (%) | 52 | 40 | 40 | 35 | 46 | 35 | 42 |
| | 202 | Right hind limb (g) | 320 | 160 | 200 | 370 | 150 | 350 | 510 |
| | | Left hind limb (g) | 400 | 410 | 400 | 440 | 290 | 800 | 700 |
| | | Weight distribution (%) | 44 | 28 | 33 | 46 | 34 | 30 | 42 |
| | 203 | Right hind limb (g) | 410 | 140 | 320 | 720 | 390 | 380 | 630 |
| | | Left hind limb (g) | 550 | 900 | 640 | 350 | 260 | 470 | 380 |
| | | Weight distribution (%) | 43 | 13 | 33 | 67 | 60 | 45 | 62 |
| | 204 | Right hind limb (g) | 490 | 520 | 630 | 250 | 660 | 630 | 660 |
| | | Left hind limb (g) | 460 | 750 | 810 | 580 | 750 | 1030 | 820 |
| | | Weight distribution (%) | 52 | 41 | 44 | 30 | 47 | 38 | 45 |
| | 205 | Right hind limb (g) | 270 | 430 | 380 | 450 | 600 | 560 | 520 |
| | | Left hind limb (g) | 260 | 880 | 700 | 760 | 710 | 570 | 840 |
| | | Weight distribution (%) | 51 | 33 | 35 | 37 | 46 | 50 | 38 |
| | 206 | Right hind limb (g) | 350 | 460 | 610 | 440 | 780 | 510 | 610 |
| | | Left hind limb (g) | 310 | 750 | 600 | 580 | 800 | 870 | 580 |
| | | Weight distribution (%) | 53 | 38 | 50 | 43 | 49 | 37 | 51 |
| | | Mean | 49.1 | 32.1 | 39.4 | 43.0 | 47.0 | 39.1 | 46.7 |
| | | SE | 1.79 | 4.21 | 2.78 | 5.36 | 3.38 | 2.82 | 3.61 |
| | | P Volum | 0.6486 | 0.9960 | 0.4310 | 0.5641 | 0.1295 | 0.5602 | 0.0053** |
| | | | | | | | | | | (%) |

(2-2) Swelling Assessment (Articular Swelling of both Hind Limbs)

Figure 10:
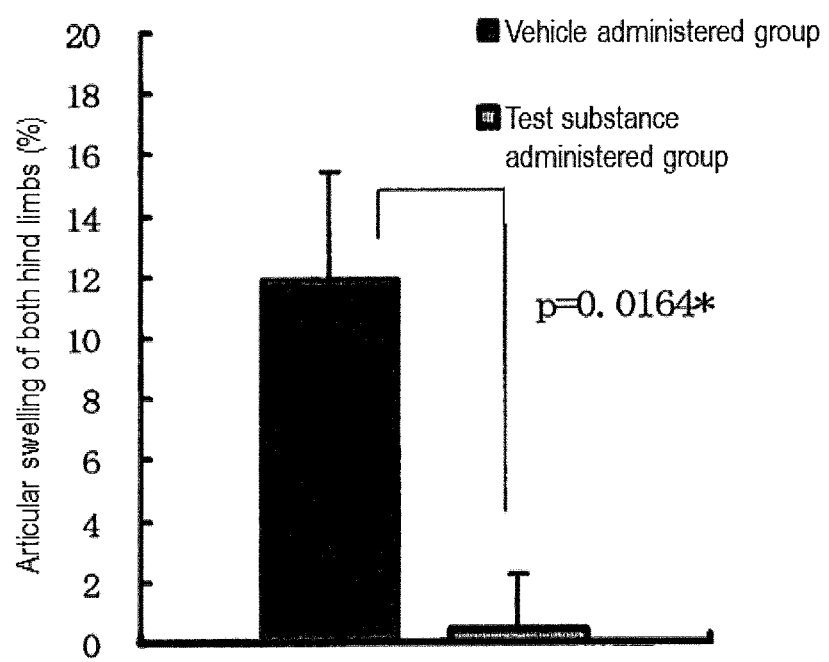
FIG. 10 shows the results of swelling assessment (articular swelling of both hind limbs). Mean±standard error, n=6; in comparison with the group 1 (the vehicle administered group) *,**; significance levels at p<0.05 and p<0.01 (the Student's t test and the Aspin-Welch t test).

Table 4 and FIG. 10 show the percentage values for articular swelling of both hind limbs on the day on which biomaterials were sampled (day 42). The width of the joint of an individual animal was measured, and the variance between groups was determined. As a result, articular swelling was inhibited more significantly in the test substance administered group, compared with the vehicle administered group (p=0.0164).

TABLE 4

Swelling assessment (articular swelling of both hind limbs)

| Group | Animal No. | Item | 4月19日 Day 42 |
|---|---|---|---|
| Vehicle administered-group | 101 | Right hind limb (mm) | 24.45 |
| | | Left hind limb (mm) | 23.98 |
| | | Swelling (%) | 1.96 |
| | 102 | Right hind limb (mm) | 25.86 |
| | | Left hind limb (mm) | 20.31 |
| | | Swelling (%) | 27.33 |
| | 103 | Right hind limb (mm) | 23.08 |
| | | Left hind limb (mm) | 21.20 |
| | | Swelling (%) | 8.87 |
| | 104 | Right hind limb (mm) | 24.37 |
| | | Left hind limb (mm) | 22.31 |
| | | Swelling (%) | 9.23 |
| | 105 | Right hind limb (mm) | 24.96 |
| | | Left hind limb (mm) | 23.00 |
| | | Swelling (%) | 8.52 |
| | 106 | Right hind limb (mm) | 26.44 |
| | | Left hind limb (mm) | 22.06 |
| | | Swelling (%) | 15.32 |
| | | Mean | 11.9 |
| | | SE | 3.54 |
| Test substance Administered-group | 201 | Right hind limb (mm) | 24.17 |
| | | Left hind limb (mm) | 24.60 |
| | | Swelling (%) | −1.75 |
| | 202 | Right hind limb (mm) | 23.75 |
| | | Left hind limb (mm) | 23.38 |
| | | Swelling (%) | 1.58 |
| | 203 | Right hind limb (mm) | 22.30 |
| | | Left hind limb (mm) | 21.50 |
| | | Swelling (%) | 3.72 |
| | 204 | Right hind limb (mm) | 21.63 |
| | | Left hind limb (mm) | 22.88 |
| | | Swelling (%) | −5.46 |
| | 205 | Right hind limb (mm) | 24.74 |
| | | Left hind limb (mm) | 23.21 |
| | | Swelling (%) | 6.59 |
| | 206 | Right hind limb (mm) | 21.36 |
| | | Left hind limb (mm) | 21.79 |
| | | Swelling (%) | −1.97 |
| | | Mean | 0.6 |
| | | SE | 1.78 |
| | | P Volum (%) | 0.0164* |

(2-3) Histopathological Evaluation

Figure 11:
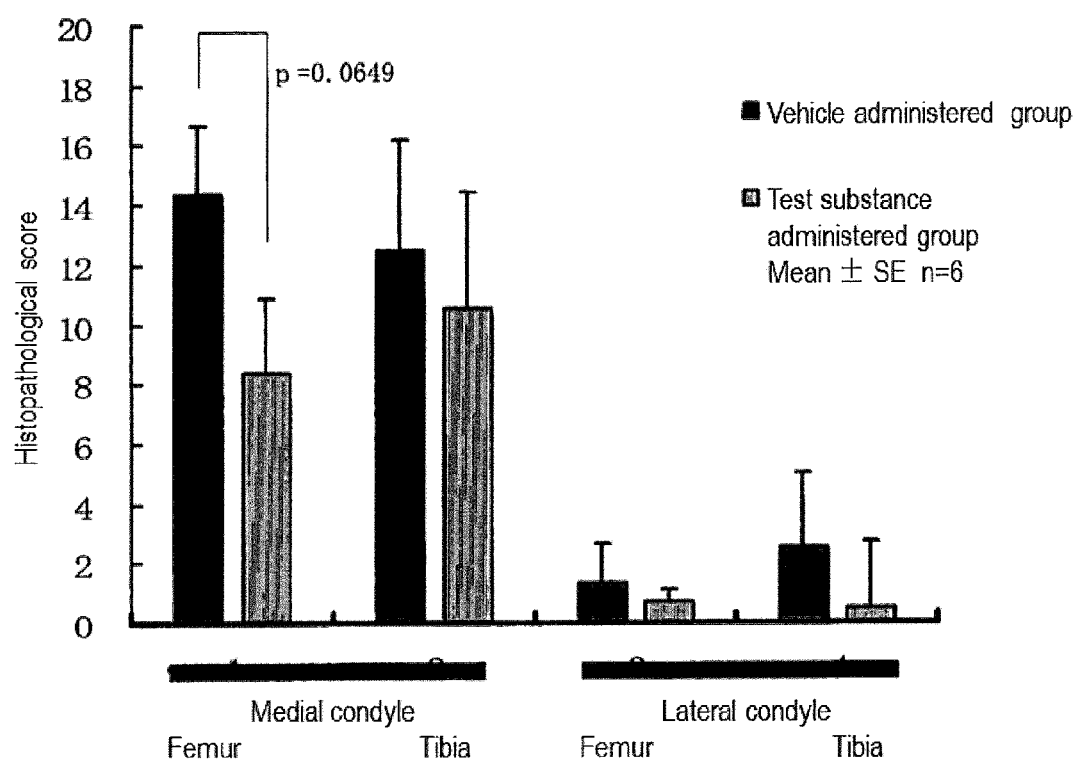
FIG. 11 shows the histopathological scores of the condyle of the femur and those of the tibia.
Figure 12:
FIG. 12 shows histopathological images of representative examples. Image A shows the vehicle administered group (Animal No. 101), in which disorganization of chondrocytes (indicated by an arrow) and cluster formation (indicated by an arrow) are observed in the joint cartilage (the medial aspect of the right femur, HE staining, magnification ×200). Image B shows the test substance administered group (Animal No. 201), in which cartilage erosion is observed (slight) in the joint cartilage (the medial aspect of the right femur, HE staining, magnification ×200). Image C shows the vehicle administered group (Animal No. 101), in which lowered proteoglycan stainability (slight) is observed in the joint cartilage (the medial aspect of the right femur, SO staining, magnification ×200). Image D shows the test substance administered group (Animal No. 201), in which no change is observed in the joint cartilage (the medial aspect of the right femur, SO staining, magnification ×200).
Figure 12:
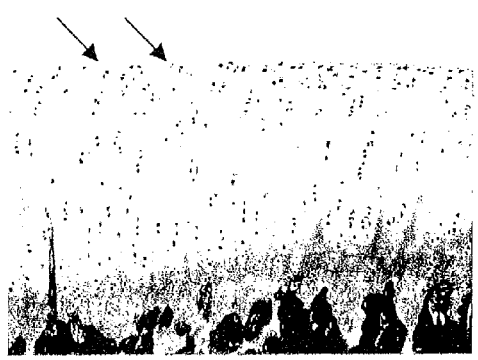
Figure 12:
Figure 12:
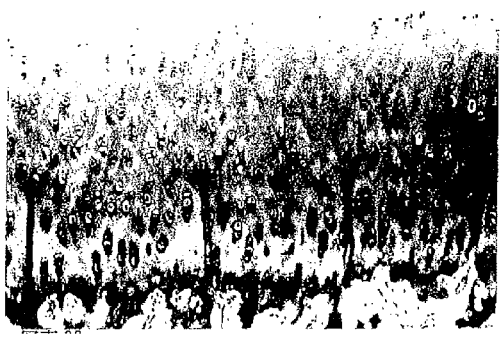

Tables 5 and 6 and FIG. 11 each show a summary of the results of histopathological tests, and FIG. 12 shows histopathological images of representative examples.

In both the vehicle administered group and the test substance administered group, substantially no damages resulting from the preparation of osteoarthritis models were observed in lateral condyles of the femur or in those of the tibia.

Concerning the medial condyle of the femur, loss of articular cartilage superficial layer, lowered proteoglycan stainability, disorganization of chondrocytes, loss of chondrocytes, and cluster formation were observed in all 6 samples of the vehicle administered group, and cartilage erosion was observed in 5 of the 6 samples thereof. The degree of cluster foimation was particularly high in all samples (mean=2.50±0.43). The histopathological scores of the observation items were 9, 21, 17, 11, 8, and 20 (mean=14.33±2.33), and slight to severe changes were observed in the articular cartilage of all samples. Concerning the medial condyle of the femur, cluster formation was observed in all 6 samples of the test substance administered group, and loss of cartilage superficial layer, cartilage erosion, and disorganization of chondrocytes were observed in 5 of the 6 samples thereof. The histopathological scores were 5, 6, 10, 3, 20, and 6 (mean=8.33±2.51), and such changes observed in 4 of the 6 samples were lesser than those observed in the vehicle administered group in the same regions. That is, the histopathological scores of the test substance administered group were lower than those of the vehicle administered group (p=0.0649).

Concerning the medial condyle of the tibia, loss of articular cartilage superficial layer, cartilage fibrillation and/or fissure, and disorganization of chondrocytes were observed in all 6 samples of the vehicle administered group, and lowered proteoglycan stainability was observed in 5 of the 6 samples thereof. The histopathological scores were 8, 27, 14, 5, 3, and 18 (mean=12.50±3.69), and slight to severe changes in the articular cartilage were observed in 4 of the 6 samples. In the test substance administered group, cartilage fibrillation and/or fissure was observed in all 6 samples, and loss of cartilage superficial layer and lowered proteoglycan stainability were observed in 5 of the 6 samples. The histopathological scores were 4, 16, 6, 1, 27, and 9 (mean=10.50±3.91).

TABLE 5

Histopathological observation (medial condyle of femur)

| | Group | | | | | | | | | | | | | | | | |
|---|---|---|---|---|---|---|---|---|---|---|---|---|---|---|---|---|---|
| | Vehicle I group | | | | | | | | Test substance group | | | | | | | | |
| Animal No. | 101 | 102 | 103 | 104 | 105 | 106 | Mean | SE | 201 | 202 | 203 | 204 | 205 | 206 | Mean | SE | P Volum |
| Loss of superficial layer | 1 | 4 | 2 | 1 | 1 | 2 | 1.83 | 0.48 | 1 | 1 | 1 | 0 | 3 | 1 | 1.17 | 0.40 | |
| Cartilage erosion | 1 | 3 | 3 | 1 | 0 | 3 | 1.83 | 0.54 | 1 | 1 | 1 | 0 | 3 | 1 | 1.17 | 0.40 | |
| Fibrillation and/or fissure | 0 | 0 | 2 | 0 | 0 | 3 | 0.83 | 0.54 | 0 | 1 | 0 | 0 | 3 | 0 | 0.67 | 0.49 | |
| Lowered proteoglycan stainability | 1 | 4 | 2 | 2 | 1 | 2 | 2.00 | 0.45 | 0 | 1 | 2 | 0 | 3 | 1 | 1.17 | 0.48 | |

TABLE 5-continued

| | | | | | | | | | | | | | | | | | |
|---|---|---|---|---|---|---|---|---|---|---|---|---|---|---|---|---|---|
| Disorganization of chondrocytes | 2 | 4 | 3 | 2 | 1 | 3 | 2.50 | 0.43 | 1 | 0 | 1 | 1 | 1 | 1 | 0.83 | 0.17 | |
| Loss of chondrocytes | 1 | 2 | 1 | 1 | 1 | 1 | 1.17 | 0.17 | 0 | 0 | 1 | 1 | 3 | 0 | 0.83 | 0.48 | |
| Exposure of subchondral bone | 0 | 0 | 0 | 0 | 0 | 2 | 0.33 | 0.33 | 0 | 0 | 0 | 0 | 2 | 0 | 0.33 | 0.33 | |
| Cluster formation | 3 | 4 | 4 | 4 | 4 | 4 | 3.83 | 0.17 | 2 | 2 | 4 | 1 | 2 | 2 | 2.17 | 0.40 | |
| Histopathological score | 9 | 21 | 17 | 11 | 8 | 20 | 14.33 | 2.33 | 5 | 6 | 10 | 3 | 20 | 6 | 8.33 | 2.51 | 0.0649 |

Histopathological observation (lateral condyle of femur)

| | Group | | | | | | | | | | | |
|---|---|---|---|---|---|---|---|---|---|---|---|---|
| | Vehicle group | | | | | | Test substance group | | | | | |
| Animal No. | 101 | 102 | 103 | 104 | 105 | 106 | 201 | 202 | 203 | 204 | 205 | 206 |
| Loss of superficial layer | 0 | 1 | 0 | 0 | 0 | 0 | 0 | 0 | 1 | 0 | 1 | 0 |
| Cartilage erosion | 0 | 1 | 0 | 0 | 0 | 0 | 0 | 0 | 1 | 0 | 1 | 0 |
| Fibrillation and/or fissure | 0 | 0 | 0 | 0 | 0 | 0 | 0 | 0 | 0 | 0 | 0 | 0 |
| Lowered proteoglycan stainability | 0 | 2 | 0 | 0 | 0 | 0 | 0 | 0 | 0 | 0 | 0 | 0 |
| Disorganization of chondrocytes | 0 | 1 | 0 | 0 | 0 | 0 | 0 | 0 | 0 | 0 | 0 | 0 |
| Loss of chondrocytes | 0 | 0 | 0 | 0 | 0 | 0 | 0 | 0 | 0 | 0 | 0 | 0 |
| Exposure of subchondral bone | 0 | 0 | 0 | 0 | 0 | 0 | 0 | 0 | 0 | 0 | 0 | 0 |
| Cluster formation | 0 | 3 | 0 | 0 | 0 | 0 | 0 | 0 | 0 | 0 | 0 | 0 |
| Histopathological score | 0 | 8 | 0 | 0 | 0 | 0 | 0 | 0 | 2 | 0 | 2 | 0 |

Observation grade: 0: None; 1: slight; 2: mild; 3: moderate; 4: severe

TABLE 6

Histopathological observation (medial condyle of tibia)

| | Group | | | | | | | | | | | | | | | | |
|---|---|---|---|---|---|---|---|---|---|---|---|---|---|---|---|---|---|
| | Vehicle group | | | | | | | | Test substance group | | | | | | | | |
| Animal No. | 101 | 102 | 103 | 104 | 105 | 106 | Mean | SE | 201 | 202 | 203 | 204 | 205 | 206 | Mean | SE | P Volum |
| Loss of superficial layer | 1 | 3 | 2 | 1 | 1 | 3 | 1.83 | 0.40 | 1 | 3 | 1 | 0 | 4 | 3 | 2.00 | 0.63 | |
| Cartilage erosion | 1 | 3 | 2 | 0 | 0 | 3 | 1.50 | 0.56 | 0 | 2 | 1 | 0 | 3 | 1 | 1.17 | 0.48 | |
| Fibrillation and/or fissure | 2 | 3 | 1 | 1 | 1 | 3 | 1.83 | 0.40 | 2 | 1 | 1 | 1 | 3 | 1 | 1.50 | 0.34 | |
| Lowered proteoglycan stainability | 1 | 4 | 2 | 1 | 0 | 2 | 1.67 | 0.56 | 1 | 4 | 1 | 0 | 4 | 1 | 1.83 | 0.70 | |
| Disorganization of chondrocytes | 2 | 4 | 2 | 1 | 1 | 2 | 2.00 | 0.45 | 0 | 2 | 1 | 0 | 4 | 1 | 1.33 | 0.61 | |
| Loss of chondrocytes | 1 | 3 | 1 | 0 | 0 | 1 | 1.00 | 0.45 | 0 | 0 | 0 | 0 | 3 | 1 | 0.67 | 0.49 | |
| Exposure of subchondral bone | 0 | 3 | 0 | 0 | 0 | 0 | 0.50 | 0.50 | 0 | 0 | 0 | 0 | 3 | 0 | 0.50 | 0.50 | |
| Cluster formation | 0 | 4 | 4 | 1 | 0 | 4 | 2.17 | 0.83 | 0 | 4 | 1 | 0 | 3 | 1 | 1.50 | 0.67 | |
| Histopathological score | 8 | 27 | 14 | 5 | 3 | 18 | 12.50 | 3.69 | 4 | 16 | 6 | 1 | 27 | 9 | 10.50 | 3.91 | 0.6991 |

Histopathological observation (lateral condyle of tibia)

| | Group | | | | | | | | | | | |
|---|---|---|---|---|---|---|---|---|---|---|---|---|
| | Vehicle group | | | | | | Test substance group | | | | | |
| Animal No. | 101 | 102 | 103 | 104 | 105 | 106 | 201 | 202 | 203 | 204 | 205 | 206 |
| Loss of superficial layer | 0 | 2 | 0 | 0 | 0 | 0 | 0 | 0 | 0 | 0 | 0 | 0 |
| Cartilage erosion | 0 | 1 | 0 | 0 | 0 | 0 | 0 | 0 | 0 | 0 | 0 | 0 |
| Fibrillation and/or fissure | 0 | 1 | 0 | 0 | 0 | 0 | 0 | 0 | 0 | 0 | 0 | 0 |

| | | | | | | | | | | | | |
|---|---|---|---|---|---|---|---|---|---|---|---|---|
| Lowered proteoglycan stainability | 0 | 4 | 0 | 0 | 0 | 0 | 1 | 1 | 0 | 0 | 1 | 0 |
| Disorganization of chondrocytes | 0 | 2 | 0 | 0 | 0 | 0 | 0 | 0 | 0 | 0 | 0 | 0 |
| Loss of chondrocytes | 0 | 2 | 0 | 0 | 0 | 0 | 0 | 0 | 0 | 0 | 0 | 0 |
| Exposure of subchondral bone | 0 | 0 | 0 | 0 | 0 | 0 | 0 | 0 | 0 | 0 | 0 | 0 |
| Cluster formation | 0 | 3 | 0 | 0 | 0 | 0 | 0 | 0 | 0 | 0 | 0 | 0 |
| Histopathological score | 0 | 15 | 0 | 0 | 0 | 0 | 1 | 1 | 0 | 0 | 1 | 0 |

Observation grade: 0: None; 1: slight 2: mild; 3: moderate; 4: severe

The invention claimed is:

1. A method for treatment of arthrosis comprising administering a compound represented by Formula (I) to a patient with arthrosis:

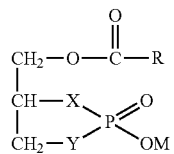

(I)

wherein R represents a linear or branched alkyl group having 1 to 30 carbon atoms, a linear or branched alkenyl group having 2 to 30 carbon atoms, or a linear or branched alkynyl group having 2 to 30 carbon atoms, which may contain a cycloalkane or aromatic ring; X and Y each independently represent an oxygen atom or a methylene group, provided that X and Y do not simultaneously represent a methylene group; and M represents a hydrogen atom or an alkali metal atom.

2. The method for treatment of arthrosis according to claim 1, wherein, in Formula (I), X and Y represent an oxygen atom.

3. The method for treatment of arthrosis according to claim 1, wherein, in Formula (I), either X or Y represents an oxygen atom, and the other represents a methylene group.

4. The method for treatment of arthrosis according to claim 1, wherein the compound represented by Formula (I) is carbacyclic phosphatidic acid of 1-oleoyl-cyclic phosphatidic acid, 1-palmitoleoyl-cyclic phosphatidic acid, or a derivative thereof.

* * * * *